(12) United States Patent
Ausiello et al.

(10) Patent No.: US 8,277,440 B2
(45) Date of Patent: Oct. 2, 2012

(54) IMPLANTABLE DEVICE FOR CONTROLLED, EXTENDED DELIVERY OF PARATHYROID HORMONE

(75) Inventors: Dennis Ausiello, Wellesley Hill, MA (US); John T. Santini, Jr., North Chelmsford, MA (US); Stephen J. Herman, Andover, MA (US); James H. Prescott, Cambridge, MA (US); Scott A. Uhland, Medford, MA (US); John M. Maloney, Cambridge, MA (US); Benjamin F. Polito, Lebanon, NH (US)

(73) Assignee: MicroCHIPS, Inc., Waltham, MA (US)

( * ) Notice: Subject to any disclaimer, the term of this patent is extended or adjusted under 35 U.S.C. 154(b) by 631 days.

(21) Appl. No.: 12/358,850

(22) Filed: Jan. 23, 2009

(65) Prior Publication Data

US 2009/0163895 A1    Jun. 25, 2009

Related U.S. Application Data

(63) Continuation of application No. 10/654,761, filed on Sep. 4, 2003, now Pat. No. 7,497,855.

(60) Provisional application No. 60/408,165, filed on Sep. 4, 2002.

(51) Int. Cl.
    *A61K 9/22* (2006.01)
(52) U.S. Cl. .................................................. 604/891.1
(58) Field of Classification Search ........ 604/890–892.1
    See application file for complete search history.

(56) References Cited

U.S. PATENT DOCUMENTS

| | | | |
|---|---|---|---|
| 4,012,496 A | 3/1977 | Schöpflin et al. | |
| 4,659,696 A | 4/1987 | Hirai et al. | |
| 4,698,328 A | 10/1987 | Neer et al. | |
| 4,822,616 A | 4/1989 | Zimmermann et al. | |
| 4,833,125 A * | 5/1989 | Neer et al. | 514/11.8 |
| 5,317,010 A * | 5/1994 | Pang et al. | 514/11.8 |
| 5,368,704 A * | 11/1994 | Madou et al. | 205/665 |
| 5,496,801 A | 3/1996 | Holthuis et al. | |
| 5,510,370 A | 4/1996 | Hock | |

(Continued)

FOREIGN PATENT DOCUMENTS

DE    19716683 C1    6/1998

(Continued)

OTHER PUBLICATIONS

Bae, et al., "Pulsatile Drug Release by Electric Stimulus," ACS Symp. Series Polymeric Drugs & Drug Admin., pp. 99-110 (1994).

(Continued)

*Primary Examiner* — Kevin C Sirmons
*Assistant Examiner* — Andrew Gilbert
(74) *Attorney, Agent, or Firm* — Sutherland Asbill & Brennan LLP

(57) ABSTRACT

Method and devices are provided for extended and controlled delivery of parathyroid hormone to a patient. The method includes implanting a medical device into the patient, the medical device comprising a substrate, a plurality of reservoirs in the substrate, a release system contained in each of the reservoirs, wherein the release system comprises parathyroid hormone; and controllably releasing a pharmaceutically effective amount of the parathyroid hormone from the reservoirs. The parathyroid hormone can be released intermittently, such as once daily over an extended period (e.g., two months, ten months, or more.). The device can further include reservoirs containing a bone resorption inhibitor or other drug for release. The devices are useful in delivering PTH for the treatment and prevention of bone loss, such as associated with osteoporosis.

8 Claims, 6 Drawing Sheets

U.S. PATENT DOCUMENTS

| | | | |
|---|---|---|---|
| 5,660,846 A * | 8/1997 | Cheikh | 424/423 |
| 5,670,514 A | 9/1997 | Audia et al. | |
| 5,797,898 A * | 8/1998 | Santini et al. | 604/890.1 |
| 5,824,646 A | 10/1998 | Fujii et al. | |
| 5,837,276 A | 11/1998 | Cheikh | |
| 5,945,412 A | 8/1999 | Fuh et al. | |
| 6,011,011 A | 1/2000 | Hageman | |
| 6,051,686 A | 4/2000 | Krstenansky et al. | |
| 6,114,658 A | 9/2000 | Roth et al. | |
| 6,123,861 A | 9/2000 | Santini, Jr. et al. | |
| 6,142,972 A | 11/2000 | Cheikh | |
| 6,239,144 B1 | 5/2001 | Galvin et al. | |
| 6,264,990 B1 | 7/2001 | Knepp et al. | |
| 6,284,730 B1 | 9/2001 | Dietrich et al. | |
| 6,294,390 B1 | 9/2001 | Barnard et al. | |
| 6,306,420 B1 | 10/2001 | Cheikh | |
| 6,349,232 B1 * | 2/2002 | Gordon | 604/20 |
| 6,376,477 B2 | 4/2002 | Schmidt et al. | |
| 6,387,711 B1 | 5/2002 | Sundaram et al. | |
| 6,417,333 B1 | 7/2002 | Bringhurst et al. | |
| 6,491,666 B1 | 12/2002 | Santini, Jr. et al. | |
| 6,527,762 B1 | 3/2003 | Santini, Jr. et al. | |
| 6,537,256 B2 | 3/2003 | Santini, Jr. et al. | |
| 6,541,450 B1 | 4/2003 | Barbier et al. | |
| 6,551,838 B2 | 4/2003 | Santini, Jr. et al. | |
| 6,590,081 B1 | 7/2003 | Zhang | |
| 6,656,162 B2 | 12/2003 | Santini, Jr. et al. | |
| 6,669,683 B2 | 12/2003 | Santini, Jr. et al. | |
| 6,740,333 B2 | 5/2004 | Beckett et al. | |
| 7,070,592 B2 * | 7/2006 | Santini et al. | 604/891.1 |
| 7,455,667 B2 * | 11/2008 | Uhland et al. | 604/890.1 |
| 7,497,855 B2 * | 3/2009 | Ausiello et al. | 604/890.1 |
| 7,510,551 B2 * | 3/2009 | Uhland et al. | 604/890.1 |
| 7,604,628 B2 * | 10/2009 | Santini et al. | 604/890.1 |
| 2002/0025929 A1 | 2/2002 | Sato | |
| 2002/0072784 A1 | 6/2002 | Sheppard, Jr. et al. | |
| 2002/0099359 A1 | 7/2002 | Santini, Jr. | |
| 2002/0107505 A1 | 8/2002 | Holladay | |
| 2002/0138067 A1 | 9/2002 | Sheppard, Jr. et al. | |
| 2002/0151776 A1 | 10/2002 | Shawgo et al. | |
| 2002/0161352 A1 | 10/2002 | Lin et al. | |
| 2002/0183721 A1 | 12/2002 | Santini, Jr. et al. | |
| 2002/0187260 A1 | 12/2002 | Sheppard, Jr. et al. | |
| 2003/0010808 A1 | 1/2003 | Uhland et al. | |
| 2003/0104590 A1 | 6/2003 | Santini, Jr. et al. | |
| 2003/0105455 A1 | 6/2003 | Santini, Jr. et al. | |
| 2004/0106953 A1 | 6/2004 | Yomtov et al. | |
| 2004/0121486 A1 * | 6/2004 | Uhland et al. | 436/174 |
| 2004/0127942 A1 | 7/2004 | Yomtov et al. | |

FOREIGN PATENT DOCUMENTS

| | | |
|---|---|---|
| WO | 0112157 | 2/2001 |
| WO | WO/01/12157 A1 * | 2/2001 |
| WO | 02056862 A2 | 7/2002 |

OTHER PUBLICATIONS

Haroun, et al., "Local Drug Delivery," Curr. Opin. Oncol. 12(3): 187-93 (2000) (abstract).

Santini, et al., "Microchip as Controlled Drug-Delivery Devices," Angew Chem. Int. Ed. Engl. 39(14): 2396-407 (2000).

Santini, et al., "Microchip Technology in Drug Delivery," Ann. Med. 32(6) 377-79 (2001).

Santini, et al., "A Controlled-Release Microchip," Nature 397(6717): 335-38 (1999).

Tao, et al., "Microfabricated Drug Delivery Systems: From Particles to Pores," Adv. Drug Deliv.. Res. 55(3): 315-28 (2003).

Horwitz, et al., "Short-Term, High-Dose Parathyroid Hormone-Related Protein asa Skeletal Anabolic Agent for the Treatment of Postmenopausal Osteoporosis," J. Endocrinol. & Metbol. 88(2): 569-75 (2003).

Kneissel, et al., Bone Tissue and its Mineralization in Aged Estrogen-Depleted Rats after Long-Term Intermittent Treatment with Parathyroid Hormone (PTH) Analog SDZ PTS 893 or Human PTH(1034) Bone 28(3): 237-50 (2001).

Liu, et al., "Long-Term Solid-State Stability of Human Parathyroid Hormone 1-34 Chloride and Acetate Salts," Human AAPS Pharmaceutica (1999),http://www.aapspharmsci.org/abstracts/AM_1999/1434.htm (abstract).

Lotinun, et al., "Differential Effects of Intermittent and Continuous Administration of Parathyroid Hormone on Bone Histomorphometry and Gene Expression," Endocrine 17(1): 29-36 (2002).

Mitlak, et al., "Sequential Effects of Chronic Human PTH (1-84) Treatment of Estrogen-Deficiency in the Rat,"J. Bone & Mineral Res. 11(4): 430-39 (1996).

Neer, et al., "Effect of Parathyroid Hormone (1-34) on Fractures and Bone Mineral Density in Postmenopausal Women with Osteoporosis," N. Engl. J. Med. 344(19): 1434-41 (2001).

Rubin, et al., "The Potential of Parathyroid Hormone as a Therapy for Osteoporosis," Int. J. Fertil. 47(3): 103-15 (2002).

Schaefer, "Pulsatile Parathyroid Hormone in Health and Disease," Novartis Found. Symp. 2000; 227: 225-39 (abstract).

Thomsen, et al., Long-Term Therapy of Ovariectomy-Induced Osteopenia with Parathyroid Hormone Analog SDZ PTS 893 and Bone Maintenance in Retired Breeder Rats,: Bone 25(5): 561-69 (1999).

* cited by examiner

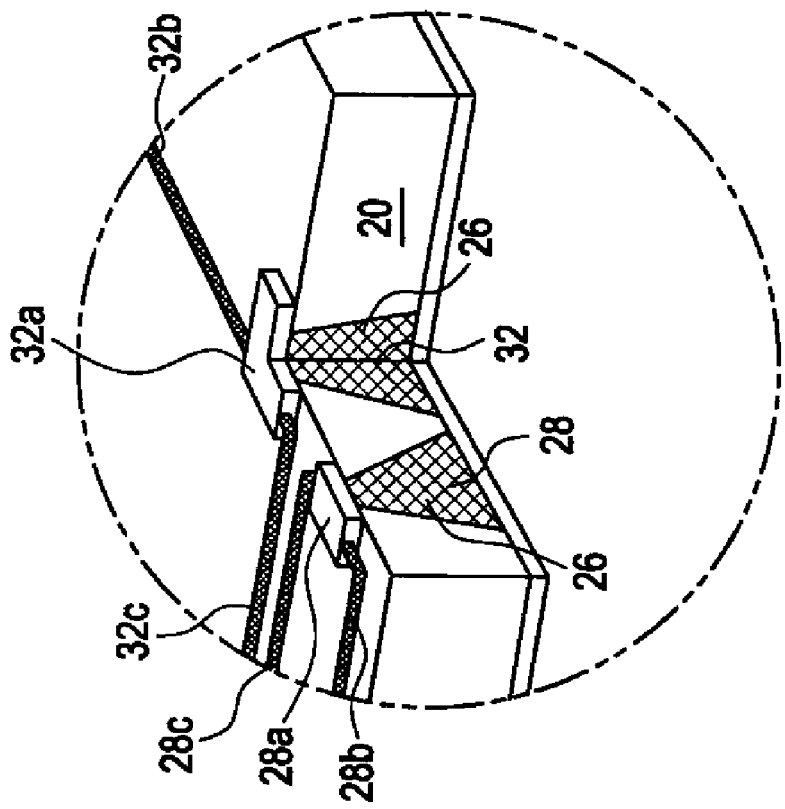
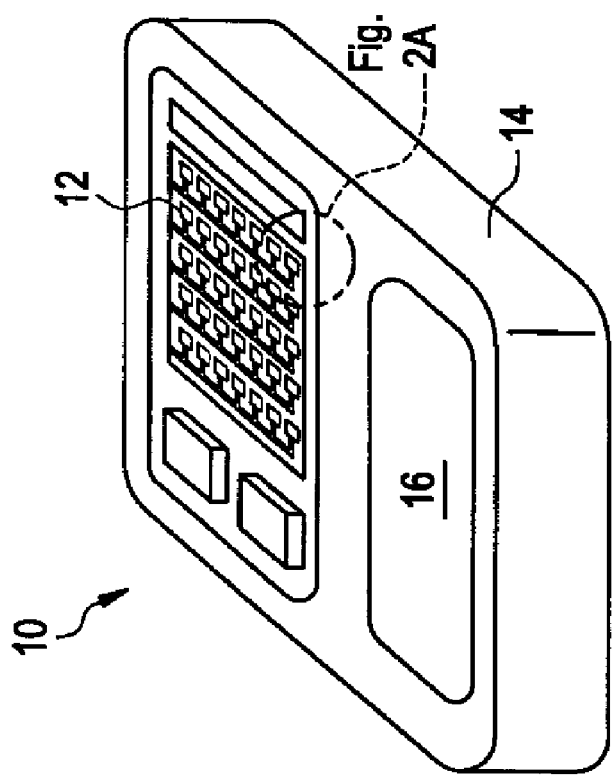

IMPLANTABLE DEVICE FOR CONTROLLED, EXTENDED DELIVERY OF PARATHYROID HORMONE

This application is a continuation of U.S. application Ser. No. 10/654,761, filed Sep. 4, 2003, now U.S. Pat. No. 7,497,855, which claims the benefit of U.S. Provisional Application No. 60/408,165, filed Sep. 4, 2002. The applications are incorporated herein by reference.

BACKGROUND OF THE INVENTION

This invention is generally in the field of methods and devices for the controlled delivery of parathyroid hormone (PTH) to patients, for example, to promote the growth and maintenance of bone tissue.

The mechanism of bone loss is not completely understood, but the disorder effectively arises from an imbalance in the formation of new healthy bone and the resorption of old bone. The bone loss includes a decrease in both mineral content and protein matrix components of the bone, and leads to an increased rate of bone fracture. These fractures, predominantly femoral bones and bones in the forearm and vertebrae, lead to an increase in general morbidity and a loss of stature and mobility, as well as an increase, in many cases, in mortality caused by complications from the fracture.

Bone loss occurs, for example, in post-menopausal women, patients who have undergone hysterectomy, patients undergoing or who have undergone long-term administration of corticosteroids, patients suffering from Cushing's syndrome, and patients having gonadal dysgenesis. Unchecked bone loss can lead to osteoporosis, a major debilitating disease whose prominent feature is the loss of bone mass (decreased density and enlargement of bone spaces) without a reduction in bone volume, producing porosity and fragility. Post-menopausal osteoporosis is associated with the large and rapid loss of bone mass due to the cessation of estrogen production by the ovaries. One source reports that ten million individuals in the United States are estimated to already have osteoporosis and almost 34 million more are estimated to have low bone mass, placing them at increased risk for the disease, and that one out of two women and one in eight men over age 50 will have an osteoporosis-related fracture in their lifetime.

PTH is involved in calcium and skeletal homeostasis. It stimulates the tubular resorption of calcium by the kidney and inhibits the reabsorption of phosphate and bicarbonate by the proximal renal tubules. PTH also affects the kidney by stimulating production of a vitamin D metabolite (1,25(OH)2D), which is an in vivo stimulator of osteoclasts and an enhancer of intestinal calcium absorption. The increase in intestinal calcium absorption following PTH stimulation is mediated by this vitamin D metabolite. In vivo, PTH stimulates osteoclastic bone resorption with the release of calcium into the circulation, and causes proliferation of osteoblasts.

With the general understanding of bone growth and its regulation, various approaches have been proposed to treat diseases involving reduction of bone mass and accompanying disorders by the administration of bone resorption inhibitors and/or anabolic agents, such as PTH. Examples of such approaches include U.S. Pat. No. 6,239,144 to Galvin et al., which discloses treating conditions associated with a lack of PTH by administering a compound having activity as a tachykinin receptor antagonist, which reportedly can increase the secretion of PTH; U.S. Pat. No. 5,670,514 to Audia et al., which discloses inhibiting bone loss by the administration of a 5α-reductase inhibitor (a benzoquinolin-3-one), alone or in combination with another bone anabolic agent, such as PTH; and U.S. Pat. No. 5,510,370 to Hock, which discloses treatment of bone loss in a patient by administering PTH sequentially, concurrently, or simultaneously with raloxifene.

It has been established that low dose, intermittent administration of PTH is associated with anabolic effects in humans, whereas higher dose, continuous administration of PTH is associated with catabolic effects. Rubin & Bilezikian, *Int. J. Fertil.* 47(3):103-15 (2002); Schaefer, *Novartis Found Symp* 227:225-39 (2000). U.S. Pat. No. 6,239,144 discloses that there is a dose dependent stimulation of the mineral apposition rate by PTH and that the result of the administration of PTH on skeletal homeostasis depends on how the hormone is administered. For the same daily dose, the bone volume shows a dose dependent increase if the daily dose of the hormone is given as one single injection. However, when the same daily dose is administered by continuous infusion with a subcutaneous mini-osmotic pump, the result is bone loss. Intermittent injection causes practically no effect on the serum calcium levels, whereas infusion causes a dose dependent increase in the serum calcium. The effects of PTH administered by these two routes on bone mineral apposition rate appeared to be the same. Once-daily injections are an undesirable means for the treatment and prevention of bone loss, because treatment and/or prophylaxis must occur over an extended period and frequent injections would be objectionable and would discourage patient compliance with the treatment. It would thus be desirable to provide alternative means for administering PTH intermittently, alone or in combination with other drugs useful in promoting bone growth and/or inhibiting bone loss.

There are myriad technologies generally referred to as providing controlled or sustained drug delivery, which deliver drug by a variety of routes. Although some controlled release methods and devices have been somewhat effective in controlling protein or peptide delivery in the body, several limitations can influence their suitability or practicality for administering a particular therapeutic agent, such as PTH. For example, many "controlled" release drug delivery systems may not provide a well-defined release profile. Other technologies may be suitable for continuous release (e.g., an ALZET™ osmotic pump), but not pulsatile release. Yet other technologies that are suitable for delivery of small molecule drugs would be unsuitable for long-term storage and delivery of fragile protein or peptide drug molecules. Such molecules may, for example, undergo degradation and denaturation associated with exposure to moisture, elevated temperatures (e.g., 37° C.), and/or by other means. Still other drug delivery systems undesirably would require periodic (frequent) replacement or refilling, or an unacceptably large size in order to provide for the administration of drug for long-term therapy.

It therefore would be desirable to provide a drug delivery system capable of accurately delivering a therapeutically and/or prophylactically effective amount of PTH, alone or in combination with other drugs. It desirably would provide well-defined pulsatile release of PTH over an extended period of time in a small, anatomically acceptable configuration, without requiring refilling of the delivery device with drug, repeated injections, or repeated replacement of part or the entire device over the course of treatment. In addition, it would be desirable for the drug delivery rate to be adjustable over the course of treatment.

SUMMARY OF THE INVENTION

Method and devices are provided for extended and controlled delivery of parathyroid hormone to a patient, for example, for the treatment and prevention of bone loss, such as associated with osteoporosis.

In one aspect, the method includes implanting a medical device into the patient, the medical device comprising a substrate, a plurality of reservoirs in the substrate, a release system contained in each of the reservoirs, wherein the release system comprises parathyroid hormone; and controllably releasing a pharmaceutically effective amount of the parathyroid hormone from the reservoirs.

In one embodiment of the method, the step of controllably releasing provides intermittent release of the parathyroid hormone. In one embodiment, the parathyroid hormone is released in a pulsatile manner, each pulse having a duration of less than four hours.

In one embodiment of the method, the parathyroid hormone is released daily in intermittent doses of between about 10 and 300 µg. In one embodiment, the daily intermittent doses are released over a period of ten months or more.

In one embodiment of the method, the pharmaceutically effective amount of the parathyroid hormone, released over a first period of time, is effective to form bone tissue. In another embodiment, the method further includes releasing a pharmaceutically effective amount of a bone resorption inhibitor, released over a second period of time, to maintain bone tissue at a level present after the first period of time. In one embodiment, the bone resorption inhibitor is selected from the group consisting of bisphosphonates, selective estrogen receptor modulators, calcitonins, vitamin D analogs, and calcium salts.

In another aspect, the implantable device for the extended, controlled delivery of parathyroid hormone to a patient comprises a substrate, a plurality of reservoirs in the substrate, a release system contained in each of the reservoirs, wherein the release system comprises parathyroid hormone, and a control means for selectively releasing a pharmaceutically effective amount of the parathyroid hormone from each of the reservoirs. In one embodiment, the device releases a pharmaceutically effective amount of parathyroid hormone once daily over a period of at least six months.

In one embodiment, the device further includes at least one reservoir which contains a second release system comprising a drug other than parathyroid hormone. For example, the drug could be an anti-resorptive agent.

In one embodiment of the device, each of the reservoirs contains between about 10 and 40 µg of parathyroid hormone for release.

In one embodiment, the device includes 300 or more reservoirs, each containing a release system comprising parathyroid hormone.

In one embodiment of the device, the release system comprises parathyroid hormone in combination with a pharmaceutically acceptable excipient. For example, the release system could include parathyroid hormone suspended in a non-aqueous vehicle. As another example, the PTH could be dried or lyophilized with an excipient that promotes re-dissolution upon release. Such an excipient could be for example, polyethylene glycol having a molecular weight between about 100 and 10,000 Daltons.

In one embodiment of the device, the control means includes reservoir caps covering the release system of the reservoirs. In one embodiment, the control means further comprises means for actively disintegrating or permeabilizing the reservoir caps. In one embodiment, the means for actively disintegrating comprises a power source for passing an electric current or potential through the reservoir caps. In a specific embodiment, the reservoir caps comprise an electrically conductive material and are electrically connected to an electrical input lead and to an electrical output lead, and the means for actively disintegrating or permeabilizing the reservoir cap comprises means for selectively applying an electrical current through the reservoir cap, via the input lead and output lead, in an amount effective to locally heat the reservoir cap to cause the reservoir cap to disintegrate to permit release of the parathyroid hormone. In another specific embodiment, the means for actively disintegrating the reservoir cap comprises a cathode, a microprocessor, a timer, and a demultiplexer, and wherein the reservoir caps each comprise an anode and upon application of an electric potential between the cathode and anode the reservoir cap disintegrates to permit release of the parathyroid hormone.

In one embodiment, the device includes a sensor, such as one that measures plasma calcium.

In another embodiment, the control means comprises two or more layers of release system having different compositions. Such an embodiment can effectively provide a passive control system for effecting pulsatile release.

In one embodiment, the device is capable of vaginal transmucosal administration of the parathyroid hormone. For example, the device can comprise a ring-shaped or rod-shaped body for fitting engagement within the vagina.

BRIEF DESCRIPTION OF THE DRAWINGS

FIG. 2 is a perspective view of another embodiment of an implantable active-release microchip device for delivery of parathyroid hormone.

DETAILED DESCRIPTION OF THE INVENTION

Figure 1A:
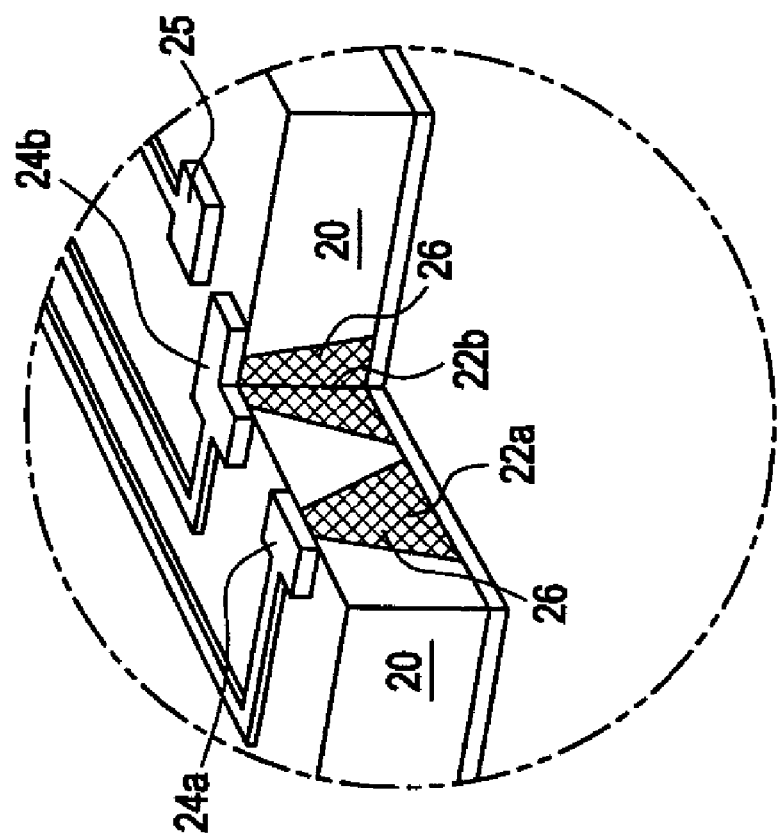
FIG. 1 is a perspective view of one embodiment of an implantable active-release microchip device for delivery of parathyroid hormone.

Implantable medical devices have been developed for the controlled delivery of parathyroid hormone. The device comprises a substrate comprising a plurality of reservoirs; a release system comprising parathyroid hormone contained in the reservoirs; and a means for controllably releasing a pharmaceutically effective amount of the parathyroid hormone from the reservoirs.

In one embodiment, the medical device comprises a microchip device. As used herein, a "microchip" is a miniaturized device fabricated using methods described in U.S. Pat. Nos. 5,797,898 and 6,123,861, to Santini, Jr. et al., as well as other methods commonly applied to the manufacture of integrated circuits and MEMS (MicroElectroMechanical Systems) such as ultraviolet (UV) photolithography, reactive ion etching, and electron beam evaporation, as known in the art, as well as MEMS methods that are not standard in making computer microchips, including those described, for example, in PCT WO 01/41736 and Madou, *Fundamentals of Microfabrication* (CRC Press, 1997), and other micromolding and micromachining and polymer forming techniques known in the art.

As used herein, the terms "comprise," "comprising," "include," and "including" are intended to be open, non-limiting terms, unless the contrary is expressly indicated.

I. Device Components and Materials

The device includes a substrate having a plurality of reservoirs, which contain the PTH and, optionally, other drug molecules. The substrate, reservoirs, reservoir caps, control circuitry, and power source are described at least in part herein and/or in U.S. Pat. Nos. 5,797,898, 6,123,861, 6,551,838, 6,491,666, and 6,527,762, as well as U.S. Patent Application Publications No. 2002/0138067, No. 2002/0072784, No. 2002/0151776, and No. 2002/0107470. In one embodiment, control of reservoir cap opening includes electro-thermal ablation techniques, as described in U.S. Pat. No. 7,455,667, which is incorporated herein by reference.

The Substrate and Reservoirs

The substrate is the structural body (e.g., part of a device) in which the reservoirs are formed, e.g., it contains the etched, machined, or molded reservoirs. A reservoir is a well, a container. MEMS methods, micromolding, and micromachining techniques known in the art can be used to fabricate the substrate/reservoirs from a variety of materials. See, for example, U.S. Pat. No. 6,123,861 and U.S. Patent Application Publication No. 2002/0107470. Examples of suitable substrate materials include metals, ceramics, semiconductors, and degradable and non-degradable polymers. Biocompatibility of the substrate material typically is preferred for in vivo device applications. The substrate, or portions thereof, may be coated, encapsulated, or otherwise contained in a biocompatible material (e.g., poly(ethylene glycol), polytetrafluoroethylene-like materials, inert ceramics, titanium, and the like) before use.

The substrate can be flexible or rigid. In one embodiment, the substrate serves as the support for a microchip device. In one example, the substrate is formed of silicon.

The substrate can have a variety of shapes, or shaped surfaces. It can, for example, have a release side (i.e., an area having reservoir caps) that is planar or curved. The substrate may, for example, be in a shape selected from disks, cylinders, or spheres. In one embodiment, the release side can be shaped to conform to a curved tissue surface or into a body lumen. In another embodiment, the back side (distal the release side) is shaped to conform to an attachment surface.

The substrate may consist of only one material, or may be a composite or multi-laminate material, that is, composed of several layers of the same or different substrate materials that are bonded together.

In one embodiment, the substrate is hermetic, that is impermeable (at least during the time of use of the reservoir device) to the molecules to be delivered and to surrounding gases or fluids (e.g., water, blood, electrolytes or other solutions).

In another embodiment, the substrate is made of a strong material that degrades or dissolves over a defined period of time into biocompatible components. Examples of biocompatible polymers include poly(lactic acid)s, poly(glycolic acid)s, and poly(lactic-co-glycolic acid)s, as well as degradable poly(anhydride-co-imides).

The substrate thickness can vary depending upon the particular device and application using the activation system described herein. For example, the thickness of a device may vary from approximately 10 µm to several millimeters (e.g., 500 µm). Total substrate thickness and reservoir volume can be increased by bonding or attaching wafers or layers of substrate materials together. The device thickness may affect the volume of each reservoir and/or may affect the maximum number of reservoirs that can be incorporated onto a substrate. The size and number of substrates and reservoirs can be selected to accommodate the quantity and volume of reservoir contents needed for a particular application, although other constraints such as manufacturing limitations or total device size limitations (e.g., for implantation into a patient) also may come into play. For example, devices for in vivo applications desirably would be small enough to be implanted using minimally invasive procedures. Alternatively, the device would be appropriately sized to be inserted into the vagina for intravaginal administration of PTH.

The substrate includes at least two and preferably tens or hundreds of reservoirs. For example, one reservoir could be provided for each daily dose of PTH required, for example, over a 6-, 8-, 10-, or 12-month course of treatment. The substrate could include, for example, 300 to 400 reservoirs, each containing a release system comprising parathyroid hormone.

In one embodiment, the reservoir has a volume equal to or less than 500 µL (e.g., less than 250 µL, less than 100 µL, less than 50 µL, less than 25 µL, less than 10 µL, etc.) and greater than about 1 nL (e.g., greater than 5 nL, greater than 10 nL, greater than about 25 mL, greater than about 50 nL, greater than about 1 µL, etc.).

Figure 4A:
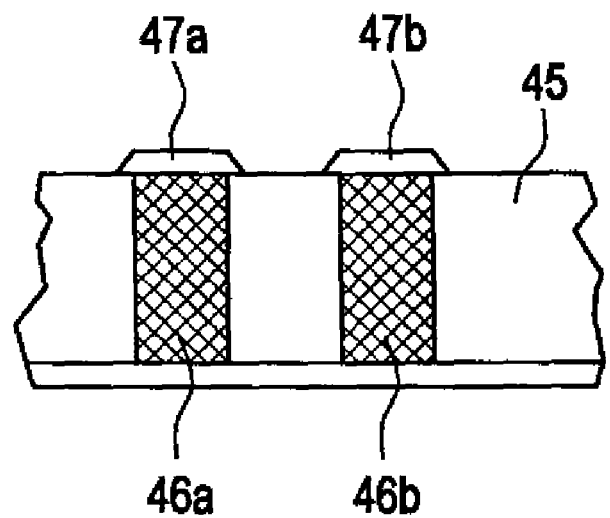
FIGS. 4A and 4B are cross-sectional views of two of the many possible embodiments of substrate/reservoir geometries: straight walled reservoirs (FIG. 4A) and combination straight and tapered walled reservoirs (FIG. 4B).
Figure 4B:
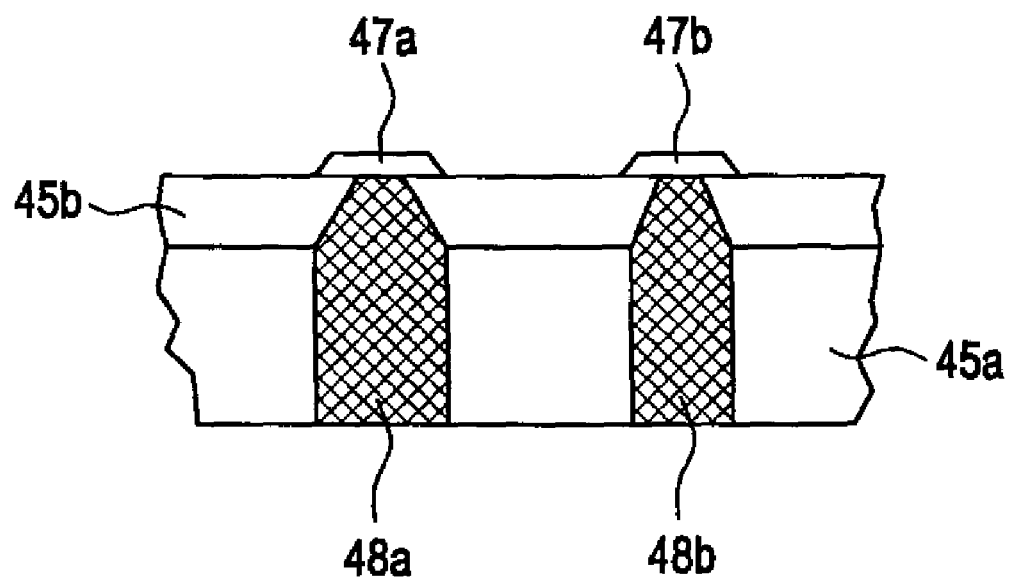

Two of the many possible embodiments of substrate/reservoir geometries are illustrated in FIGS. 4A-4B. The embodiment shown in FIG. 4A shows substrate 45 having reservoirs 46a and 46b, which are covered by reservoir caps 47a and 47b, respectively. Reservoirs 46a and 46b have straight, i.e. non-tapered, walls. The embodiment shown in FIG. 4B shows a laminate substrate, composed of lower portion 45a and upper portion 45b, which has reservoirs 48a and 48b, which are covered by reservoir caps 47a and 47b, respectively. Reservoirs 48a and 48b have a combination of straight walls in the lower portion 45a of the substrate and tapered walls in the upper portion 45b of the substrate.

Drug and Release System

The release system comprises a pharmaceutical formulation of the parathyroid hormone. As used herein, "release system" includes the situations where the PTH molecules are in pure form (e.g., as a lyophilized powder), in suspension, in solution, or in a matrix formed of biodegradable material or another material which releases incorporated PTH molecules by diffusion or disintegration of the matrix. The release system can, for example, include excipients that modulate the rate of release of PTH.

Parathyroid Hormone

As used herein, the term "parathyroid hormone" or "PTH" includes the complete human hormone (hPTH 1-84); fragments of the hormone responsible for bone growth promotion, such as hPTH 1-34 and hPTH 1-38, and analogs in which the amino acid sequence is modified slightly, yet retain bone growth promotion properties, such as PTH-RP; and synthetic and/or recombinant biologically active peptide derivatives of parathyroid hormone (e.g., hPTH(1-28)), such as described in U.S. Pat. No. 6,417,333 to Bringhurst et al. The PTH may be native or synthesized by chemical or recombinant means.

The PTH may or may not be in lyophilized form, depending upon the desired formulation and storage requirements. For example, the PTH could be provided in a lyophilized salt form, such as a chloride or acetate (e.g., as hPTH(1-34)Cl or PTH(1-34)OAc), which could be sealed in the reservoirs under nitrogen gas with low water content, without excipient. Alternatively, lyophilized PTH can be suspended in a non-solvent (e.g., non-aqueous) vehicle. In another embodiment, the PTH can be incorporated into micelles or liposomes.

In one embodiment, the release system comprises PTH dried or lyophilized with an excipient that promotes re-dissolution upon release. Such a composition would accelerate the rate of release (i.e., reduce the pulse duration). An example of a suitable excipient in this embodiment is polyethylene glycol having a molecular weight between about 100 and 10,000 Daltons.

Excipient

In one embodiment, the release system includes PTH in (e.g., in a mixture with) a pharmaceutically acceptable excipient. As used herein, the term "excipient" is used broadly to include virtually any suitable drug delivery vehicle.

The excipient may be a solvent or non-solvent for the PTH to prepare a solution or suspension of the PTH, respectively. The solvent or non-solvent may be aqueous or non-aqueous, so long as the PTH is substantially stable in the solution or suspension during storage in the reservoirs of the drug delivery device and for the useful lifetime of the device.

In one embodiment, the PTH is provided in suspension with a non-aqueous vehicle suitable for stable storage. Preferred pharmaceutically acceptable excipients include non-aqueous vehicles suitable for suspension and stable storage of PTH at 37° C. for several months, preferably a year or more. The non-aqueous vehicle could be an anhydrous, aprotic, hydrophobic, non-polar liquid, with low reactivity to PTH. Representative examples of non-aqueous vehicles include biocompatible perhalohydrocarbons or unsubstituted saturated hydrocarbons. Examples of these include perfluorodecalin, perfluorobutylamine, perfluorotripropylamine, perfluoro-N-methyldecahydroquindine, perfluorooctohydroquinolidine, perfluoro-N-cyclohexylpyrilidine, perfluoro-N,N-dimethylcyclohexyl methylamine, perfluorodimethyl-adamantane, perfluorotri-methylbicyclo (3.3.1) nonane, bis(perfluorohexyl)ethene, bis(perfluorobutyl) ethene, perfluoro-1-butyl-2-hexyl ethene, tetradecane, methoxyflurane and mineral oil. See, e.g., U.S. Pat. No. 6,264,990 to Knepp et al.

In one embodiment, the PTH is provided in a solution. An example of a non-aqueous (anhydrous) solvent that may be suitable is DMSO (dimethyl sulfoxide).

In another embodiment, the release system comprises PTH dried or lyophilized with an excipient that would promote re-dissolution upon release, such as polyethylene glycol having a molecular weight between about 100 and 10,000 Daltons.

Other suitable pharmaceutically acceptable excipients include various carriers approved for parenteral administration, including saline, Ringer's solution, Hank's solution, and solutions of glucose, lactose, dextrose, mannitol, ethanol, glycerol, albumin, and the like. The release system may optionally include stabilizers, antioxidants, antimicrobials, preservatives, buffering agents, surfactants, dessicants, and other additives useful for storing and releasing PTH from the reservoirs in vivo.

PTH Dosage

The devices can be used to deliver essentially any medically indicated dosage of PTH. In one embodiment, PTH dosages are between 0.5 and 1.0 μg/(kg·day). In one embodiment, the PTH advantageously is released in daily pulsatile doses of between 10 and 300 μg. For example, each reservoir could contain a single dose, e.g., about 20 μg PTH (1-34) or about 100 to 200 μg PTH (1-84) in a suitable formulation. Release dosages can be varied by a number of techniques, for example, by providing different quantities of drug among different reservoirs (some reservoirs contain 20 μg of PTH, and others contain 10, 15, or 40 μg of PTH) and/or by combining various numbers of reservoirs to form a single dose (e.g., simultaneously opening two reservoirs each containing 10 μg of PTH).

Other Drugs

While at least two of the reservoirs (and more likely tens to hundreds of reservoirs) will contain PTH, reservoirs may contain release system consisting or comprising other (non-PTH) drugs for release. These additional drugs may be in the same reservoirs as the PTH or in different reservoirs. Representative examples of these other drugs include bone resorption inhibitors, such as bisphosphonates (e.g., alendronate, risedronate sodium), estrogen, selective estrogen receptor modulators (e.g., raloxifene HCl), calcitonins, vitamin D analogs, and calcium salts. In an alternative embodiment of the method for administering PTH, the PTH is delivered (e.g., subcutaneously or intravaginally) from the implanted medical device described herein and the other drug, e.g., an anti-resorptive agent, is administered orally using a conventional oral dosage form. In either approach (other drug administered from implanted device or orally), the PTH and the other drug(s) may be administered sequentially, concurrently, or simultaneously.

These other drugs, alone or in combination with a pharmaceutically acceptable excipient, may be in pure solid, liquid (e.g., solution or suspension), or gel form, or mixed with other materials that affect the release rate and/or time. The drugs may be in the form of solid mixtures including amorphous and crystalline mixed powders, monolithic solid mixtures, lyophilized powders, and solid interpenetrating networks. The drugs may, for example, be in the form of liquid mixtures, including solutions, emulsions, colloidal suspensions, and slurries, or in the form of gel mixtures, including hydrogels.

Reservoir Caps

As used herein, the term "reservoir cap" includes a membrane or other structure suitable for separating the contents of a reservoir from the environment outside of the reservoir. It generally is self-supporting across the reservoir opening, although caps having additional structures to provide mechanical support to the cap can be fabricated. Selectively removing the reservoir cap or making it permeable will then "expose" the contents of the reservoir to the environment (or selected components thereof) surrounding the reservoir. In preferred embodiments, the reservoir cap is selectively disintegrated. As used herein, the term "disintegrate" is used broadly to include without limitation degrading, dissolving, rupturing, fracturing or some other form of mechanical failure, as well as a loss of structural integrity due to a chemical reaction (e.g., electrochemical degradation) or phase change (e.g., melting) in response to a change in temperature, unless a specific one of these mechanisms is indicated. In one specific embodiment, the "disintegration" is by an electrochemical activation technique, such as described in U.S. Pat. No. 5,797,898. In another specific embodiment, the "disintegration" is by an electro-thermal ablation technique, such as described in U.S. Pat. No. 7,455,667.

In active release devices, the reservoir cap generally includes any material that can be disintegrated or permeabilized in response to an applied stimulus, e.g., electric field or current, magnetic field, change in pH, or by thermal, chemical, electrochemical, or mechanical means.

In one embodiment, the reservoir cap is a thin metal film and is impermeable to the surrounding environment (e.g., body fluids or another chloride containing solution). In one variation, a particular electric potential is applied to the metal reservoir cap, which is then oxidized and disintegrated by an electrochemical reaction, to release the drug from the reservoir. Examples of suitable reservoir cap materials include gold, silver, copper, and zinc.

In another variation, the reservoir cap is heated (e.g., using resistive heating) to cause the reservoir cap to melt and be displaced from the reservoir to open it. This latter variation could be used, for example, with reservoir caps formed of a metal or a non-metal material, e.g., a polymer. In yet another variation, the reservoir cap is formed of a polymer or other material that undergoes a temperature-dependent change in permeability such that upon heating to a pre-selected temperature, the reservoir is rendered permeable to the drug and bodily fluids to permit the drug to be released from the reservoir through the reservoir cap.

In still another embodiment, the reservoir cap is formed of a conductive material, such as a metal film, through which an electrical current can be passed to electrothermally ablate it, as described in U.S. Pat. No. 7,455,667. Representative examples of suitable reservoir cap materials include gold, copper, aluminum, silver, platinum, titanium, palladium, various alloys (e.g., Au/Si, Au/Ge, Pt—Ir, Ni—Ti, Pt—Si, SS 304, SS 316), and silicon doped with an impurity to increase electrical conductivity, as known in the art. In one embodiment, the reservoir cap is in the form of a thin metal film. In one embodiment, the reservoir cap is part of a multiple layer structure, for example, the reservoir cap can be made of multiple metal layers, such as a multi-layer/laminate structure of platinum/titanium/platinum. The reservoir cap is operably (i.e. electrically) connected to an electrical input lead and to an electrical output lead, to facilitate flow of an electrical current through the reservoir cap. When an effective amount of an electrical current is applied through the leads and reservoir cap, the temperature of the reservoir cap is locally increased due to resistive heating, and the heat generated within the reservoir cap increases the temperature sufficiently to cause the reservoir cap to be electrothermally ablated (i.e., ruptured).

In passive release devices, the reservoir cap is formed from a material or mixture of materials that degrade, dissolve, or disintegrate over time, or that do not degrade, dissolve, or disintegrate, but are permeable or become permeable to molecules or energy. Representative examples of reservoir cap materials include polymeric materials, and non-polymeric materials such as porous forms of metals, semiconductors, and ceramics. Passive semiconductor reservoir cap materials include nanoporous or microporous silicon membranes.

In one embodiment, the release system containing the molecules to be delivered is covered by a degradable cap material that is nearly impermeable to the molecules. The time of release of the molecules from the reservoir will be limited by the time necessary for the cap material to degrade or dissolve. In another embodiment, the cap material is non-degradable and is permeable to the molecules to be delivered. The physical properties of the material used, its degree of crosslinking, and its thickness will determine the time necessary for the molecules to diffuse through the cap material. If diffusion out of the release system is limiting, the cap material delays the onset of release. If diffusion through the cap material is limiting, the cap material determines the release rate of the molecules in addition to delaying the onset of release.

In one embodiment, a passive, layered release system to provide pulsatile release is used in combination with an actuatable reservoir cap.

Figure 3:
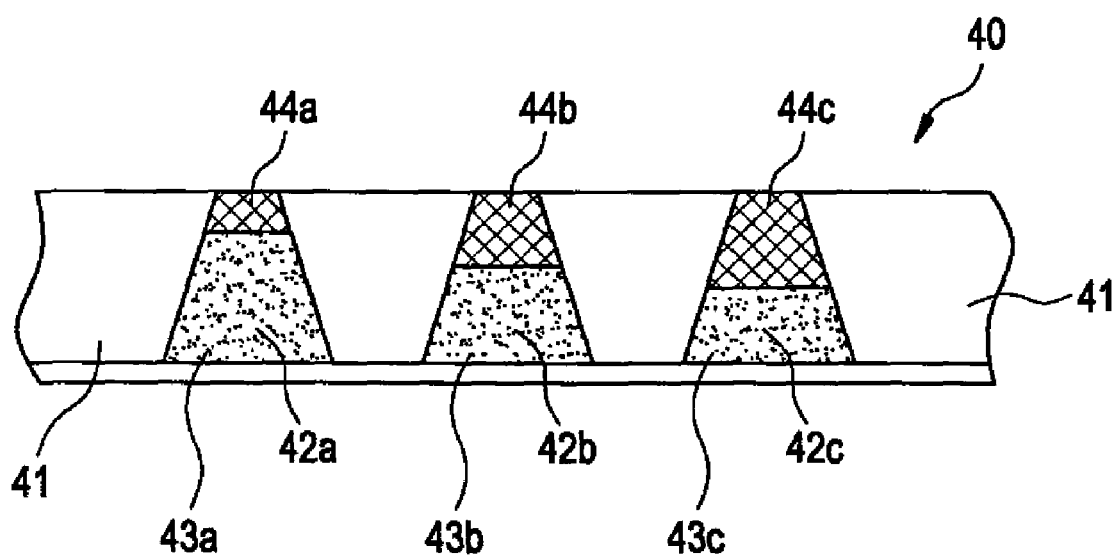
FIG. 3 is a cross-sectional view of one embodiment of a passive release microchip device for delivery of parathyroid hormone.

FIG. 3 illustrates a microchip device for the passive release of parathyroid hormone. It shows device 40 which includes substrate 41 having three reservoirs 42a, 42b, and 42c, which contain, respectively, release system 43a, 43b, and 43c, which are covered respectively, by bioerodible or biodegradable reservoir caps 44a, 44b, and 44c. In this embodiment, the thickness of the reservoir caps is different for each reservoir cap to provide different times of PTH release.

Any combination of passive and/or active release reservoir cap can be present in a single microchip device. For example, the reservoir cap can be removed by electrothermal ablation to expose a passive release system that only begins its passive release after the reservoir cap has been actively removed. Alternatively, a given substrate can include both passive and active release reservoirs.

Controlling Release

The device preferably is provided with a control means to control the time at which the PTH or other drug is released from the device, and into the patient's body. At least for PTH, the control means should provide intermittent release, for example, daily over a period of months (e.g., 2, 6, 10, or preferably 12, months or more). The particular features of the control means depend on the mechanism of reservoir cap activation described herein.

For example, the control means can include the hardware, electrical components, and software needed to control and deliver the electric current from a power source to selected reservoir caps for actuation (i.e., opening). The control means can include an input source, a microprocessor, a timer, a demultiplexer (or multiplexer), and a power source. As used herein, the term "demultiplexer" also refers to multiplexers. The power source provides energy to activate the selected reservoir, i.e. trigger release of drug from the particular reservoir desired for a given dose. For example, the operation of the reservoir opening system can be controlled by an on-board microprocessor (e.g., the microprocessor is within an implantable or insertable device). The microprocessor can be programmed to initiate the disintegration or permeabilization of the reservoir cap in response at a pre-selected time or in response to one or more of signals or measured parameters, including receipt of a signal from another device (for example by remote control or wireless methods) or detection of a particular condition using a sensor such as a biosensor. In another embodiment, a simple state machine is used, as it typically is simpler, smaller, and/or uses less power than a microprocessor. The device can also be activated or powered using wireless means, for example, as described in U.S. 20020072784 A1 to Sheppard et al.

In one embodiment, the device includes a substrate having a two-dimensional array of reservoirs arranged therein, a release system comprising PTH contained in the reservoirs, anode reservoir caps covering each of the reservoirs, cathodes positioned on the substrate near the anodes, and means for actively controlling disintegration of the reservoir caps. The means includes a power source and circuitry to control and deliver an electrical potential energy drives a reaction between selected anodes and cathodes. Upon application of a potential between the electrodes, electrons pass from the anode to the cathode through the external circuit causing the anode material (reservoir cap) to oxidize and dissolve into the surrounding fluids, exposing the release system containing the PTH for delivery to the surrounding fluids, e.g., in vivo. The microprocessor directs power to specific electrode pairs through a demultiplexer as directed by a PROM, remote control, or biosensor.

In another embodiment, the activation energy initiates a thermally driven rupturing or permeabilization process, for example, as described in PCT WO 01/12157. For example, the means for controlling release can actively disintegrate or permeabilize a reservoir cap using a resistive heater. The resistive heater can cause the reservoir cap to undergo a phase change or fracture, for example, as a result of thermal expansion of the reservoir cap or release system, thereby rupturing the reservoir cap and releasing the PTH from the selected reservoir. The application of electric current to the resistor can be delivered and controlled using components as described above for use in the electrochemical disintegration embodiment. For example, a microprocessor can direct current to select reservoirs at desired intervals.

In yet another embodiment, control means controls electro-resistive ablation of the reservoir cap. For example, the drug delivery device could include a reservoir cap formed of an electrically conductive material, which prevents the PTH from passing out from the device; an electrical input lead connected to the reservoir cap; an electrical output lead connected to the reservoir cap; and a control means to deliver an effective amount of electrical current through the reservoir cap, via the input lead and output lead, to locally heat and rupture the reservoir cap to release the PTH. In one embodiment, the reservoir cap and conductive leads are formed of the same material, where the temperature of the reservoir cap increases locally under applied current because the reservoir cap is suspended in a medium that is less thermally conductive than the substrate. Alternatively, the reservoir cap and conductive leads are formed of the same material, and the reservoir cap has a smaller cross-sectional area in the direction of electric current flow, where the increase in current density through the reservoir cap causes an increase in localized heating. The reservoir cap alternatively can be formed of a material that is different from the material forming the leads, wherein the material forming the reservoir cap has a different electrical resistivity, thermal diffusivity, thermal conductivity, and/or a lower melting temperature than the material forming the leads. Various combinations of these embodiments can be employed.

In the case where the reservoir cap is the same material as the leads, the lead-reservoir cap layer is continuous and there are no connections or interfaces. In the case where the reservoir cap and the lead are of dissimilar compositions, the interface/connection is an intermetallic junction. The connections to the power source can be made by traditional IC means, flip-chip, wirebonding, soldering, and the like.

Microelectronic device packages are typically made of an insulating or dielectric material such as aluminum oxide or silicon nitride. Low cost packages can also be made of plastics or reinforced epoxies (similar to those used in making printed circuit boards). Their purpose is to allow all components of the device to be placed in close proximity and to facilitate the interconnection of components to power sources and to each other, while protecting the electronics from the environment. Implanted microchip device packages will need to be hermetically sealed, e.g., in a titanium encasement, which essentially exposes only the reservoir caps.

The control means can include a microprocessor, a timer, a demultiplexer, and an input source (for example, a memory source, a signal receiver, or a biosensor), and a power source. The timer and demultiplexer circuitry can be designed and incorporated directly onto the surface of the microchip during electrode fabrication, or may be incorporated in a separate microchip. The criteria for selection of a microprocessor are small size, low power requirement, and the ability to translate the output from memory sources, signal receivers, or biosensors into an address for the direction of power through the demultiplexer to a specific reservoir on the microchip device. Selection of a source of input to the microprocessor such as memory sources, signal receivers, or biosensors depends on the microchip device's particular application and whether device operation is preprogrammed, controlled by remote means, or controlled by feedback from its environment (i.e. biofeedback).

A microprocessor is used in conjunction with a source of memory such as erasable programmable read only memory (EPROM), a timer, a demultiplexer, and a power source such as a battery or a biofuel cell. A programmed sequence of events including the time a reservoir is to be opened and the location or address of the reservoir is stored into the EPROM by the user. When the time for exposure or release has been reached as indicated by the timer, the microprocessor sends a signal corresponding to the address (location) of a particular reservoir to the demultiplexer. The demultiplexer routes an input, such as an electric potential or current, to the reservoir addressed by the microprocessor.

In one embodiment of a passive release embodiment, the means for controllably releasing comprises the release system having different layers of disintegratable materials such that pulsatile release of the parathyroid hormone is provided by disintegration of the layers. For example, a single pulse from each reservoir using multiple reservoirs effectively provides a pulsatile release profile. Alternatively, a pulsatile release profile can be provided from a single reservoir, for example, by incorporating several layers of a release system and other materials into a single reservoir. In either case, the reservoir caps can be formed from a material that degrades or dissolves over time, or does not degrade or dissolve, but is permeable to the PTH molecules to be delivered. These materials are preferably polymeric materials. Materials can be selected for use as reservoir caps to give a variety of degradation rates, dissolution rates, or permeabilities to enable the release of PTH molecules from different reservoirs at different times and, in some cases, different rates. To obtain different release times (amounts of release time delay), caps can be formed of different polymers (e.g., that dissolve at varying rates), the same polymer with different degrees of crosslinking, or a UV polymerizable polymer. In the latter case, varying the exposure of this polymer to UV light results in varying degrees of crosslinking and gives the cap material different diffusion properties or degradation or dissolution rates. Another way to obtain different release times is by using one polymer, but varying the thickness of that polymer. Thicker films of some polymers result in delayed release time. Any combination of polymer, degree of crosslinking, or polymer thickness can be modified to obtain a specific release time or rate.

The layered release system technique described above for use in achieving a pulsatile PTH release profile advantageously and surprisingly has been found to aid in avoiding undesirable phenomena during release (e.g., aggregation, precipitation of PTH). It was found that when trying to release a solution of PTH at a low pH (e.g., pH 3) through a tiny reservoir opening (e.g., a square having 50 micron sides) and into a physiological solution (pH 7), the PTH could precipitate and block the reservoir opening. While not being bound by any theory, it is believed that this phenomena was due to the salts (e.g., MW ~60) in the PTH solution diffusing into the physiological solution at a rate that exceeded the rate of diffusion of the PTH (e.g., MW ~4000) due, for example, to the molecular weight (MW) dependence of diffusion rate, to such an extent that the pH of the PTH solution increased to a point exceeding that required to keep the PTH in solution. (For example, at pH 3, the PTH has a solubility of about 100 µg/ml and at pH 7, the PTH has a solubility of about 20 µg/ml.)

Figure 5:
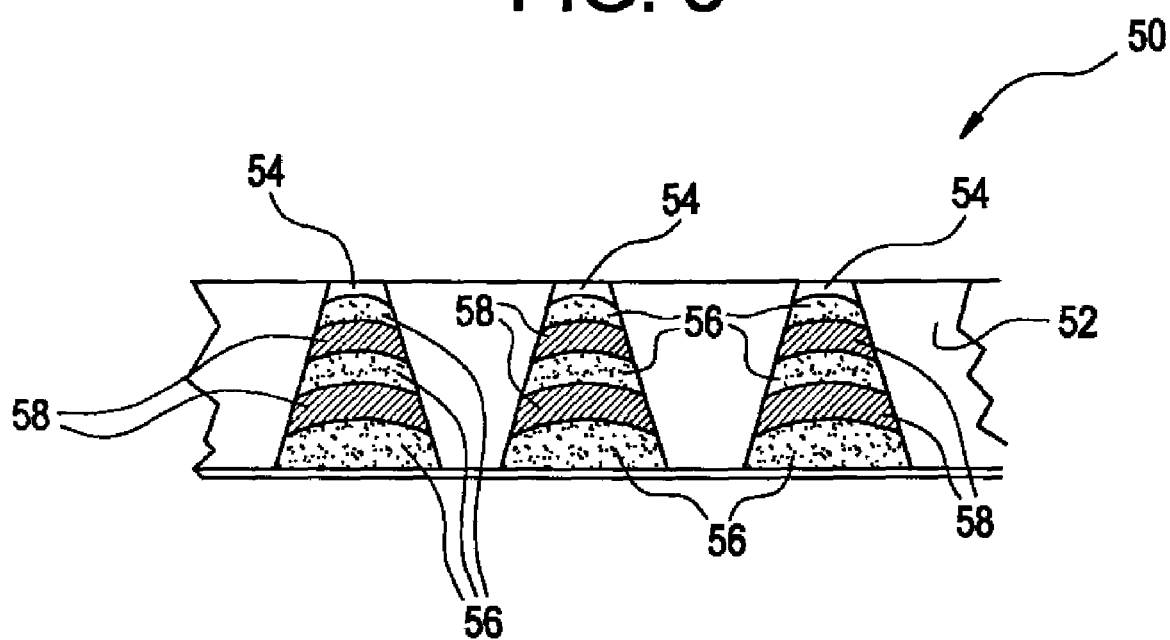
FIG. 5 is a cross-sectional view of one embodiment of a passive release device substrate having a layered release system for controlling release as well as for controlling aggregation and precipitation of PTH.

By varying the concentration of the PTH to account for the mass diffusion rate differences, precipitation of the PTH can be avoided, e.g., to keep the PTH concentration (and/or pH) at the reservoir opening sufficiently low. It is believed that the same technique could be used to prevent aggregation/precipitation of other proteins or peptides released from a microreservoir system. For example, the release system in a reservoir could comprise layers of different drug content and/or excipient which could effect release rates and localized drug concentrations within and adjacent the reservoir during release. In one embodiment, the reservoir release system comprises alternating layers of drug and non-drug materials. FIG. 5 illustrates device 50 comprising substrate 52 having reservoirs covered by reservoir caps 54 and containing a release system that consists of PTH-containing layers 56 which are alternated with excipient layers 58. In another embodiment, the layers comprises different concentrations of PTH, in accordance with the varying diffusion distances (and varying cross-sectional areas for reservoirs having tapered walls) in the reservoir. In such layering techniques, a solid fill is needed, for example, where layers comprises a matrix material (e.g., in the form of a sol or gel) having drug dispersed therein. In one embodiment, the matrix material is a water-soluble, inert polymer, such as polyethylene glycol (PEG), which is solid at 37° C.

Sensors

In an optional embodiment, the microchip device includes a sensor or sensing component. For example, the sensor or sensing component can be located in a reservoir or can be attached to the device substrate. The sensor can operably communicate with the device, e.g., through a microprocessor, to control or modify the drug release variables, including dosage amount and frequency, time of release, effective rate of release, selection of drug or drug combination, and the like. The "sensing component" includes a component utilized in measuring or analyzing the presence, absence, or change in a chemical or ionic species, energy, or one or more physical properties (e.g., pH, pressure). Types of sensors include biosensors, chemical sensors, physical sensors, or optical sensors. Further examples of such sensors and sensor components are described in PCT WO 01/64344. The sensor or sensing component detects (or not) the species or property at the site of in vivo implantation (e.g., in a bodily fluid or tissue), and further may relay a signal to the microprocessor used for controlling release from the microchip device, as detailed below. Such a signal could provide feedback on and/or finely control the release of parathyroid hormone.

In one embodiment, the sensor measures plasma calcium levels in the patient and modulates release of PTH or other drugs in response to the measured calcium level, and the amount of parathyroid hormone released from the microchip is dependent on the level of plasma calcium detected by such a sensor. An example of a calcium sensor is described in Van Den Burg, et al., "An ISFET-Based Calcium Sensor Using a Photopolymerized Polysiloxane Membrane," *Sensors & Actuators* B, vol. 4, pp. 235-38 (1991).

The microchip device may also factor in other information in determining the amount and timing of PTH release. For example, bone density and hydroxyproline levels in the urine may be clinical indicators for PTH treatment, and the presence of hyperthyroidism or fluctuation in calcium homeostasis may relate to the increased calcium levels detected. Such information can be transmitted to the microchip device, preferably wirelessly, from other sensors and/or from a physician inputting the information derived, for example, from diagnostic tests performed on the patient.

There are several different options for receiving and analyzing data obtained with devices located in the microchip devices. Active microchip devices may be controlled by local microprocessors or remote control. Biosensor information may provide input to the controller to determine the time and type of activation automatically, with human intervention, or a combination thereof.

Typically, the operation of the microchip system will be controlled by an on-board (i.e. within the package) microprocessor. The output signal from the device, after conditioning by suitable circuitry if needed, will be acquired by the microprocessor. After analysis and processing, the output signal can be stored in a writeable computer memory chip, and/or can be sent (e.g., wirelessly) to a remote location away from the microchip. Power can be supplied to the microchip system locally by a microbattery or remotely by wireless transmission.

In one embodiment, the microchip device includes one or more biosensors (which may be sealed in reservoirs until needed for use) that are capable of detecting and/or measuring signals within the body of a patient. As used herein, the term "biosensor" includes sensing devices that transduce the chemical potential of an analyte of interest into an electrical signal (e.g., an ion selective field effect transistor or ISFET), as well as electrodes that measure electrical signals directly or indirectly (e.g., by converting a mechanical or thermal energy into an electrical signal). For example, the biosensor may measure intrinsic electrical signals (EKG, EEG, or other neural signals), pressure, temperature, pH, or loads on tissue structures at various in vivo locations. The electrical signal from the biosensor can then be measured, for example by a microprocessor/controller, which then can transmit the information to a remote controller, another local controller, or both. For example, the system can be used to relay or record information on the patient's vital signs or the implant environment, such as drug concentration.

Figure 1:
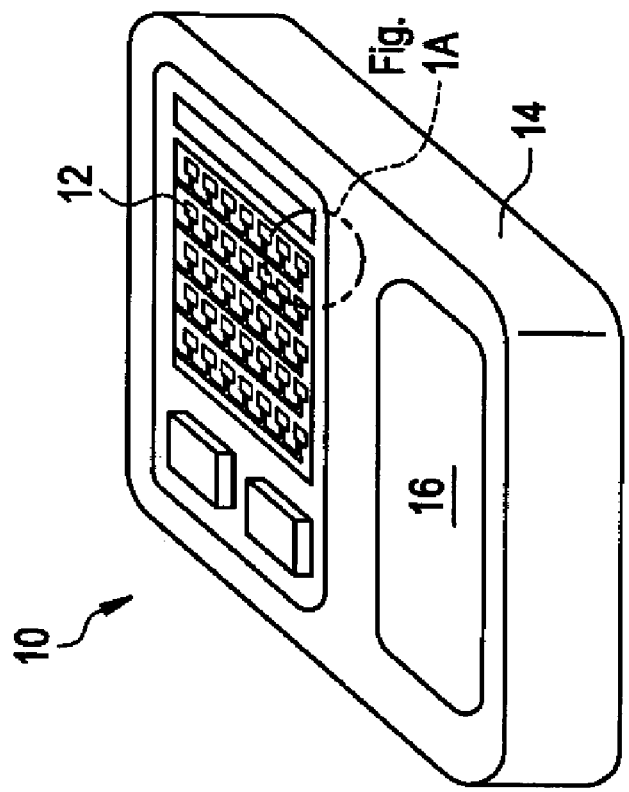

One embodiment of an implantable active-release microchip device for delivery of PTH is illustrated in FIG. 1. It shows, in a perspective view, microchip device 10, which includes substrate/reservoir portion 12 in a biocompatible package 14, such as a titanium encasement. The package 14 further includes battery 16 and other device electronics. FIG. 1 also shows a close-up, in a perspective and partial cross-sectional view, of a portion of substrate/reservoir portion 12. The close-up illustrates two reservoirs 22a and 22b in substrate 20, which contain release system 26 comprising parathyroid hormone. The reservoirs 22a and 22b are covered by anodic reservoir caps 24a and 24b, respectively, which could be opened by an electrochemical degradation mechanism upon application of an electric potential between a cathode 25 and the anode reservoir caps.

Another embodiment of an implantable active-release microchip device for delivery of PTH is illustrated in FIG. 2. As in FIG. 1, it shows, in a perspective view, microchip device 10, which includes substrate/reservoir portion 12 in a biocompatible package 14, such as a titanium encasement. The package 14 further includes battery 16 and other device electronics. The close-up view in FIG. 2 also shows, in a perspective and partial cross-sectional view, a portion of substrate/ reservoir portion 12, illustrating two reservoirs 28 and 32 in substrate 20, which contain release system 26 comprising parathyroid hormone. In this embodiment, the reservoirs 28 and 32 are covered by reservoir caps 28a and 32a, respectively. Reservoir cap 28a is electrically connected to electrical input lead 28b and to electrical output lead 28c, and reservoir cap 32a is electrically connected to electrical input lead 32b and to electrical output lead 32c. These reservoir caps could be opened via a thermal rupturing mechanism by passing an electric current through the caps in an amount effective to locally heat the cap material and rupture the reservoir cap.

II. Methods of Making the Medical Devices

Methods for making the substrate, reservoirs, and reservoir opening/activation components are described for example in U.S. Pat. Nos. 5,797,898; 6,123,861; U.S. Patent Application Publication No. 2002/0107470; U.S. Patent Application Publication No. 2002/0151776, and U.S. Patent Application Publication No. 2002/0183721, as well as U.S. Pat. No. 7,455,667, which are hereby incorporated by reference in their entirety. In one embodiment, a MEMS technique is used to make the substrate, reservoirs, and reservoir caps. In another embodiment, standard machining techniques, such as drilling or laser machining are used to make the substrate and reservoirs.

In yet another embodiment, soft lithography, microcontact printing, or the like is used. For example, these techniques can be useful for forming leads and reservoir caps on non-planar substrates. See, e.g., U.S. Pat. Nos. 6,180,239; 5,951,881; 6,355,198; and 6,518,168.

In one embodiment, the assembly of a complete microchip drug delivery device involves a number of packaging steps, including (1) attachment of electrical leads to the substrate, (2) filling of the reservoirs with a release system comprising PTH, (3) sealing the reservoirs, (4) integration with electronic components and power sources, and (5) placing the microchip(s) and associated components within a single biocompatible enclosure or "package." The package optionally may be conformally coated with parylene or an inert ceramic material (see e.g., U.S. Patent Application Publication No. 2002/0187260). In some embodiments, insulating or dielectric materials are deposited over the reservoir cap, leads, or entire surface of the device by methods such as chemical vapor deposition (CVD), electron or ion beam evaporation, sputtering, or spin coating to protect the device or enhance biostability/biocompatibility. Examples of such materials include oxides, nitrides, carbides, diamond or diamond-like materials, or fluorocarbon films. Methods for assembling, sealing, and packaging microchip chemical delivery devices useful herein are described, for example, in U.S. Pat. No. 6,123,861, U.S. Patent Application Publication No. 2002/0119176 and No. 2003/0010808, which are expressly incorporated herein by reference.

In one embodiment, the step of reservoir sealing and the step of formation of a reservoir cap over the reservoir opening can be combined. This is particularly useful for devices in which the reservoirs are filled and released from the same side, for example, in embodiments where the reservoirs are formed in a substrate without penetrating through the entire thickness of the substrate. In an alternative embodiment, the reservoir is filled from an opening in the end of the reservoir distal the reservoir cap, and then this opening is permanently sealed.

III. Uses of the Medical Devices

The microchip devices and release methods described herein can be used to deliver (i.e., administer) parathyroid hormone to a patient for a variety of treatments. For example, the devices and methods can be used to reduce the incidence of bone fractures, defects, and disorders which result from weakened bones due to as osteoporosis, osteoarthritis, Paget's disease, osteohalisteresis, osteomalacia, bone loss resulting from multiple myeloma and other forms of cancer, bone loss resulting from side effects of other medical treatment (such as steroids), and age-related loss of bone mass. In addition, the microchip device could be used for strengthening a bone graft, for treating prosthetic ingrowth such as promoting bone ingrowth into a bone prosthesis, for treating a bone fracture, or for treating childhood idiopathic bone loss in a child.

As used herein, the term "patient" refers to a living vertebrate animal such as a mammal (e.g., human) in need of treatment, i.e., in need of bone repair, augmentation, or replacement. The term "treatment" refers to (1) providing a patient with an amount of a substance sufficient to act prophylactically to prevent the development of a weakened and/or unhealthy state; (2) providing a patient with a sufficient amount of a substance so as to alleviate or eliminate a disease state and/or the symptoms of a disease state, and a weakened and/or unhealthy state; (3) providing a patient with an amount of a substance sufficient to promote bone formation; or (4) providing combinations of such substances.

In one embodiment, the microchip device is implanted into the patient for long-term delivery of PTH, alone or in combination with other drugs. "Long term" refers to release over an extended period (e.g., between 1 week and 3 years, between 6 weeks and 2 years, between 3 months and 1 year, etc.). The microchip device can be implanted in vivo using standard surgical or minimally invasive implantation techniques, e.g., via a catheter, at any suitable site. Preferred sites include subcutaneous pectoral or abdominal sites. Depending upon the particular administration route or implantation site, the microchip device can be used for local, regional, or systemic delivery of PTH.

In one embodiment, the medical device is adapted to deliver the PTH by the vaginal route. The medical device could use active release or could rely solely on passive release to deliver the PTH. A particular advantage of using the vaginal route of administration for delivering PTH is that deployment of the device is not surgical. No implantation procedure is necessary; rather the device is manually inserted into the vagina of the patient, not unlike a tampon or conventional vaginal ring device. In one embodiment, the device would be designed for more frequent replacement than would be desirable for a subcutaneous device. In such an embodiment, the device would not need to hold as much PTH as the device for subcutaneous implantation. In an active embodiment, the control electronics and power source could also be simplified, thereby reducing the cost of the device. In one embodiment, the microchip device could be made to be very small and release daily doses of PTH for one or two months, after which time the device could be removed and replaced with a new one. If appropriate, treatment could be halted immediately at any time by simply removing the device.

In one embodiment, the microchip device includes or is combined with a polymeric (e.g., medical grade silicone rubber) body, such as a strip-, rod-, or torus-shaped device. The body can be, for example, in the form of a vaginal ring-like device (see e.g., U.S. Patent Application Publication No. 20020161352, U.S. Pat. Nos. 4,822,616, and 4,012,496, for description of vaginal rings that can be modified for use herein). A patient or a caregiver can manually place the device into the vagina, where the device remains secured in place by contact (e.g., frictional engagement) with the vaginal walls. In one embodiment, the vaginal ring device could include a polymeric coating that is bioadhesive to mucosal surfaces. Preferably no suturing or other more permanent securing means would be required. In one technique, the vaginal ring/microchip device could include an expandable portion that expands upon insertion to enhance the frictional engagement with the vaginal walls. In another technique, the vaginal ring/microchip device is selected to have a size appropriate for a particular patient.

Figure 6:
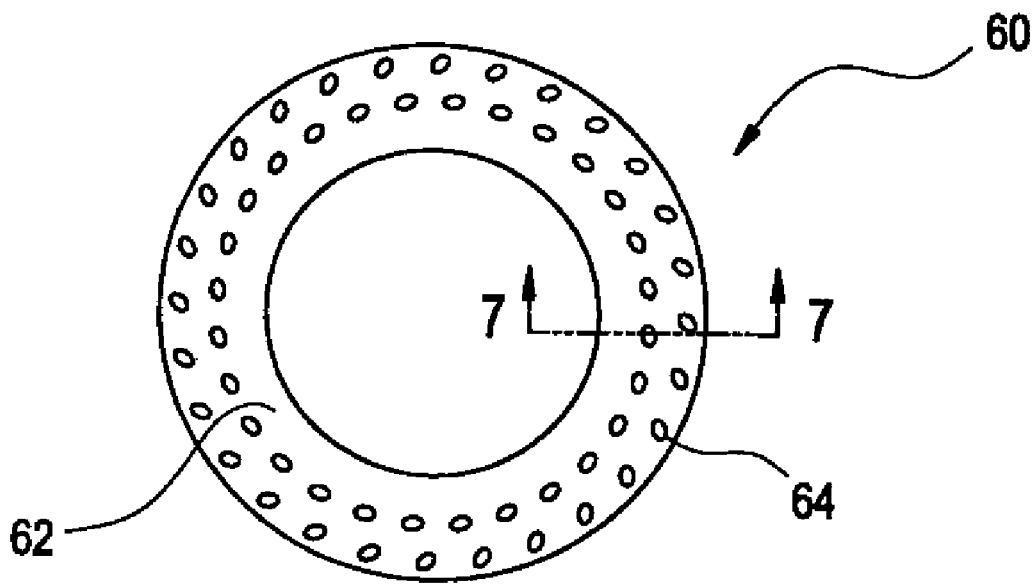
FIG. 6 is a plan view of one embodiment of the medical device described herein for intravaginal delivery of PTH.
Figure 7:
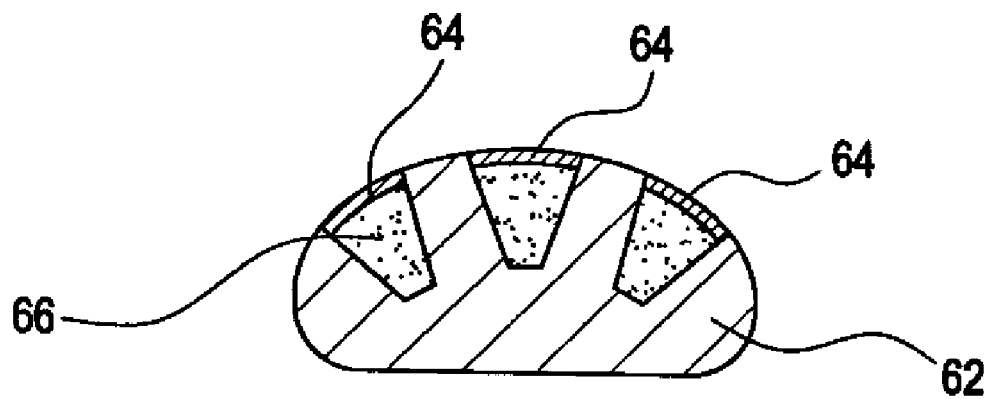
FIG. 7 is a cross-sectional view of the device shown in FIG. 6.

In yet another embodiment, an array of discrete microreservoirs are fabricated directly into a vaginal ring body (which serves as the substrate), as illustrated in FIGS. 6-7. The substrate is (integral with) the attachment body. These figures show device 60 having ring-shaped body 62 in which a plurality of reservoirs containing a PTH formulation 66 are located. The reservoirs are sealed by (generic) reservoir caps 64. The reservoir caps may be opened by any of a number of passive or active techniques described herein. Active control means can be embedded (e.g., within a compartment) in the ring-shaped body. The body can be a multilayer structure, for example it could have a rigid core portion and a soft polymeric shell.

In a preferred embodiment, the drug-release side of the microchip device is positioned toward and in contact with the mucosal tissues of the vaginal wall. This facilitates transport of the drug from a reservoir, upon opening, to moist vaginal tissues, enabling the drug to diffuse into the capillaries and other small blood vessels in the tissue, for systemic delivery. Accordingly, in one embodiment of the PTH formulation for vaginal administration, the PTH composition is formulated with a penetration enhancer or absorption promoter to enable such penetration, absorption, transfer or transport through the mucosa.

Once the microchip device is placed at the site that PTH delivery (i.e. release) is desired, the PTH can be controllably released from one or more of the reservoirs, either actively or passively, in a pharmaceutically effective amount at the desired dosing schedule. The term "pharmaceutically effective" refers to that amount which effects the formation and differentiation of bone.

Generally, each reservoir is loaded with between about 10 and about 300 µg of parathyroid hormone. In a preferred therapy, the microchip device delivers daily doses (pulses) of 20 µg/day of PTH (1-34) for one year, in order to grow bone, to restore lost bone mass.

The width (i.e., duration) of each pulse dose of PTH is selected to be a therapeutically effective period. In one embodiment, the duration of each pulse is less than four hours (e.g., less than three hours, less than two hours, less than one hour).

In a typical treatment method, the patient would first receive PTH by injection for the first one or two months of therapy to ensure that the patient experiences no adverse reactions (e.g., hypercalcemia) to the PTH treatment. Once it has been established that the patient is accepting treatment with adverse reaction, then the microchip device for PTH delivery would be implanted into the patient. The microchip device would then provide administration of PTH, obviating the need for injections going forward. In one embodiment, a single microchip device provides least all of the PTH doses required over the course of therapy. For example, the device could contain enough PTH to provide daily doses for between about 10 months and about 12 months.

After the PTH treatment regimen is completed (e.g., after about one year), a treatment with one or more anti-resorptive agents is typically begun. For example, the treatment could include daily doses of a chronic bone loss inhibitor, for up to five years. Optionally, the same device further provides some or all of the doses of anti-resorptive agent. In other methods, the PTH is administered from the implanted microchip device, and the anti-resorptive agent is administered by another route suitable for the selected anti-resorptive agent, such as orally or by parental injection.

In one embodiment, which could be implanted, a single, non-refillable microchip device is provided with at least a year's supply of PTH for delivery. For example, the microchip device could have a substrate provided with a 400-reservoir array, with each reservoir containing a single dose, e.g., about 20 µg PTH (1-34) or about 100 to 200 µg PTH (1-84) in a suitable formulation.

For example, in an active-release embodiment, the microchip device can be controlled by a pre-programmed microprocessor to open a one or a portion of the reservoirs intermittently (that is, a different one or more reservoirs after each period) to effect release intermittently, e.g., in a pulsatile manner. In other variations, the microprocessor (and thus release) is controlled by a sensor, e.g., a biosensor, or by remote control.

In one embodiment of a passive release microchip device, the PTH can be controllably released using reservoir caps formed of a biodegradable material (e.g., a polymer, such as PLGA). Release times can be controlled and varied by altering the thickness of the reservoir cap, the composition of the reservoir cap (e.g., degree of crosslinking, etc.), or both.

In other embodiments, another drug is released before, simultaneously with, or following one or more releases of PTH. For simultaneous release, the other drug can be contained in the same reservoirs that contain the PTH or the other drug can be contained in one or more separate reservoirs. The other drug can be controllably released in a continuous or intermittent manner. For example, PTH and raloxifene may be administered sequentially, concurrently, or simultaneously as a single composition to the patient. If administered sequentially, the period between the administration of PTH and raloxifene will typically be one week to one year, and optimally, one week to six months. In a preferred administration scheme, the patient will, after administration of PTH, with or without raloxifene, be administered raloxifene after cessation of administration of PTH.

In one embodiment, the PTH is released intermittently from the microchip device during a period between 6 and 24 months, and then once PTH administration has been completely, a bone resorption inhibitor is released during a period between about 6 and 36 months.

Methods of using microchip devices for controlled release of drug and other molecules is further described in U.S. Pat. Nos. 5,797,898, 6,123,861, 6,551,838, 6,491,666, and 6,527,762, and U.S. Patent Application Publications No. 2002/0138067, No. 2002/0072784, No. 2002/0151776, and No. 2002/0107470.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. An implantable device for controlled delivery of parathyroid hormone to a patient in need thereof comprising:
   a substrate having a plurality of discrete reservoirs;
   a quantity of parathyroid hormone contained in each of the reservoirs;
   a plurality of reservoir caps separating said quantity of parathyroid hormone from an environment outside of the reservoirs, and preventing the parathyroid hormone from being released from the implantable device; and
   an electrical input lead and an output lead, which leads are continuous with, or connected by an intermetallic junction to, each of the reservoir caps and configured to pass an electric current from a power source through said each reservoir cap and thereby cause the reservoir cap to rupture by electrothermal ablation and permit the parathyroid hormone to be released from the implantable device,
   wherein each of said reservoir caps comprises a multi-layer metal structure.

2. The device of claim 1, wherein the multi-layer structure comprises platinum and titanium.

3. The device of claim 1, wherein the parathyroid hormone in a dried or lyophilized form.

4. The device of claim 1, which is adapted to release a pharmaceutically effective amount of the parathyroid hormone from the reservoirs in daily intermittent doses of between about 10 and 300 µg.

5. The device of claim 1, which is adapted to release the parathyroid hormone once daily over a period of at least six months.

6. The device of claim 1, wherein the parathyroid hormone is recombinantly synthesized.

7. The device of claim 1, wherein the parathyroid hormone is a fragment of the complete human hormone that promotes bone growth responsible for bone growth promotion or an analog thereof in which the amino acid sequence is modified yet retains its bone growth promotion property.

8. The device of claim 1, wherein the parathyroid hormone consists essentially of hPTH 1-34, hPTH 1-38, or hPTH 1-28.

* * * * *